United States Patent [19]

Cheesman et al.

[11] 4,422,548

[45] Dec. 27, 1983

[54] SURGICAL SPONGE COUNTER AND BLOOD LOSS DETERMINATION SYSTEM

[75] Inventors: Barbara E. Cheesman, Cornwall; Raza Alikhan, Oakville, both of Canada

[73] Assignee: Ritmed Limited

[21] Appl. No.: 340,261

[22] Filed: Jan. 18, 1982

[51] Int. Cl.³ .................... A61B 19/00; A61F 13/00; B65D 30/22; B65D 85/00; G01G 19/00
[52] U.S. Cl. .................... 206/370; 206/438; 150/52 R; 177/1; 177/245
[58] Field of Search ............... 206/363, 362, 370, 438; 150/52 R, 1; 220/20; 177/1, 245

[56] References Cited

U.S. PATENT DOCUMENTS

| | | | |
|---|---|---|---|
| 2,359,372 | 10/1944 | Leader | 150/1 |
| 2,778,398 | 1/1957 | Edwards | 150/152 R |
| 3,397,804 | 8/1968 | Davis | 220/20 |
| 3,613,899 | 10/1971 | Schleicher et al. | 206/438 |
| 3,749,237 | 7/1973 | Dorton | 206/438 |
| 4,190,153 | 2/1980 | Olsen . | |
| 4,234,086 | 11/1980 | Dorton | 206/362 |
| 4,295,537 | 10/1981 | McAvinn et al. . | |
| 4,312,447 | 1/1982 | McWilliams | 206/370 |
| 4,361,231 | 11/1982 | Patience | 206/362 |

Primary Examiner—William T. Dixson, Jr.
Attorney, Agent, or Firm—Donald E. Hewson

[57] ABSTRACT

Apparatus for handling soiled surgical sponges is provided, where at least one or two arrays of pouches are formed along the length of a strip of thermoplastic material, where the pouches are oriented so as to be contiguous one to another at adjoining sides, or an adjoining top or bottom, or both. Each of the pouches may be provided with a flap to close the pouch, whereby the risk of contamination is reduced. The thermoplastic strip having the array of pouches is adapted for suspension along its top edge, and may thereby be associated with an operating room kick bucket directly, or indirectly, or with a holding frame, and also with a weighing scale, whereby soiled surgical sponges may be counted, weighed and disposed of with a minimum of handling.

8 Claims, 5 Drawing Figures

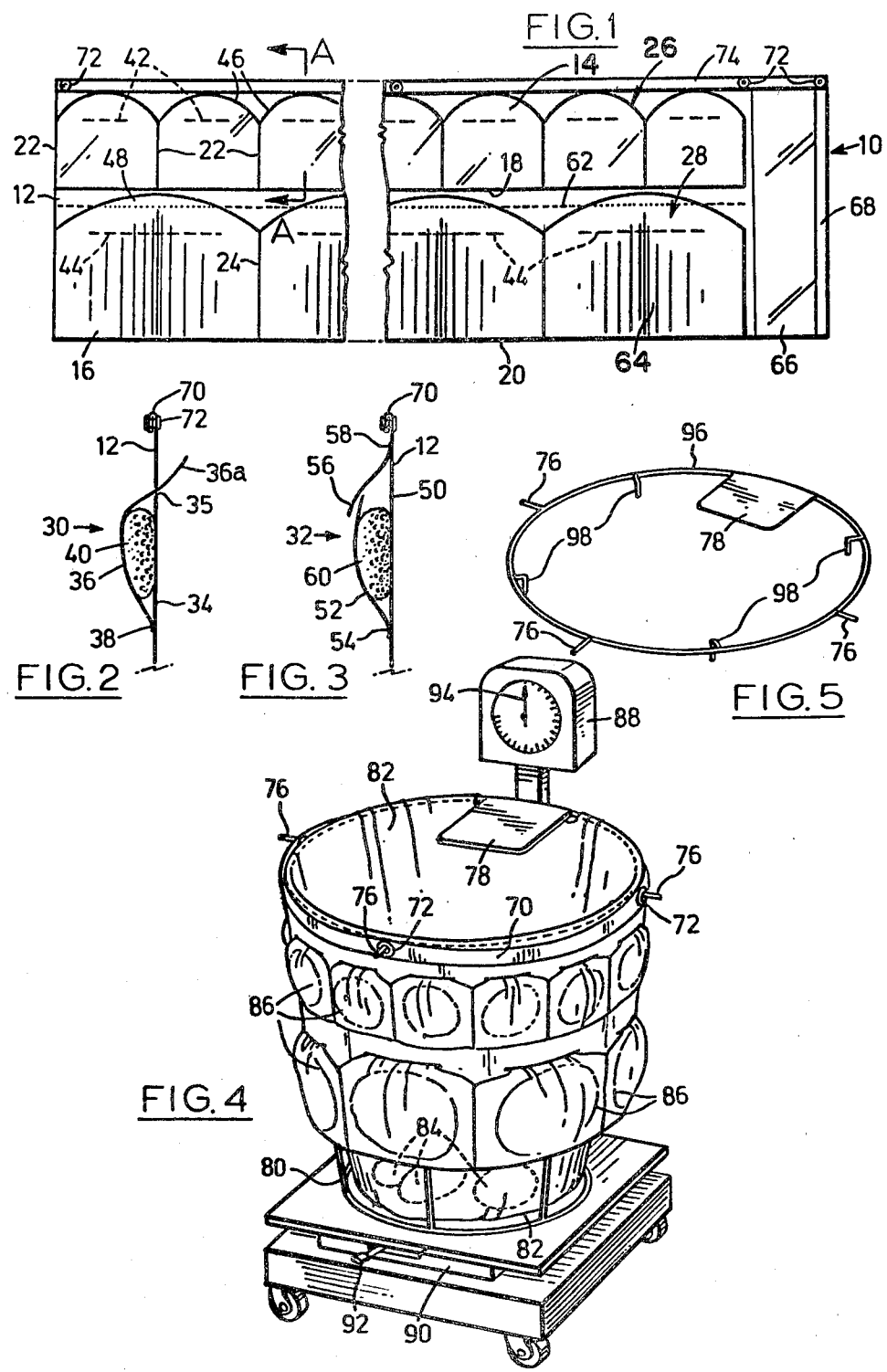

SURGICAL SPONGE COUNTER AND BLOOD LOSS DETERMINATION SYSTEM

FIELD OF THE INVENTION

This invention relates to apparatus for handling soiled sponges from surgical procedures in an operating room. In particular, the present invention relates to a disposable array of pouches into which soiled surgical sponges may be placed, so that a sponge count may be easily attended to, and at the same time blood loss may be determined either by visual inspection or by weighing, without the necessity of excessive handling or counting of the soiled surgical sponges. Indeed, the present invention also relates to a system whereby soiled surgical sponges may be counted, weighed and disposed of, without excessive handling or counting; and the present invention provides such a system which is substantially self-contained.

BACKGROUND OF THE INVENTION

During surgical procedures in an operating room of a hospital, nearly always there are surgical sponges used, whereby blood which comes as a consequence of bleeding caused during the surgical procedure is captured by the surgical sponges. The sponges are discarded, usually by being placed into a kick bucket, and thereafter they are counted and disposed of.

A constant risk during surgical procedures is that there may be a mis-count, whereby the risk that a surgical sponge may accidentally be left in a wound or opening caused by the surgical procedure, greatly increases. Morevoer, it is the duty of the operating room personnel to determine if there is excessive loss of blood by the patient, during the surgical procedure.

Thus, most operating rooms have very strict sponge count requirements, whereby the number of sponges in the operating room is counted before the surgical procedure, a count is maintained and updated during the surgical procedure, and a final count is made before termination of the surgery and closing of the wound or opening. The continuing count of soiled sponges is generally the responsibility of one, non-sterile, nurse in the operating room, who may not enter the sterile area, and among whose responsibilities are included that of sorting and counting the surgical sponges.

Moreover, there is a further responsibility of the nursing and anesthesiology persons assisting at the surgical procedure to determine whether there is excessive blood loss by the patient. For those reasons, it is convenient that the soiled surgical sponges should be maintained in one general place, so that skilled surgical personnel may, by visual inspection, determine whether there may have been excessive blood loss or not. However, it is often desirable that there should be a more accurate method by which blood loss may be determined, and that is to weigh the soiled surgical sponges and to deduct from the result the weight of the sponges when unused (either dry or with saline solution substantially wrung out therefrom), whereby quite accurate determination of blood loss may be made.

Still further, it is a general concern in operating rooms that contamination should be maintained at the lowest possible level, so that the risk of post-operative infection may be substantially precluded. Thus, it is desirable that as much as possible the soiled surgical sponges should be contained and preferably covered.

In most cases, at least small surgical sponges (about 10 cm. square) are disposed of after use—i.e., they are only used once. However, larger surgical sponges such as laparotomy sponges may, in some hospitals, be recovered following the surgical procedure for washing and re-use. In any event, however, the correct count of all such sponges used in a surgical procedure must be determined, either before the sponges are disposed of or returned to laundry and sanitizing procedures for re-use.

A number of procedures have been used in the past, for counting and maintaining the count of surgical sponges being used. Such procedures have included laying the sponges on the floor of the operating room—usually on a folded towel—or the use of certain commercially available products. However, none of the procedures used, to date, have adequately provided for an accurate weighing of the soiled surgical sponges for determination of blood loss, while at the same time providing ease of access to the soiled sponges, ease of access to the storage for the soiled sponges, and ease of count and re-count.

For example, an article about blood loss determination in the Journal of the Association of Operating Room Nurses, (AORN) for June 1981, volume 33, No. 7, by Darden, at pages 1368 to 1380 discusses ways by which blood loss may be determined by inspection of soiled surgical sponges. That article points out that blood loss may range from moderate to severe, and notes particularly that small amounts of blood loss in infants and children may result in critical conditions for the patient. Moreover, the article suggests that sponge tallies and weighing of the sponges should be made at least every 15 minutes, otherwise the determination of blood loss may be quite inaccurate because of the drying blood in the sponges.

However, although the article suggests that sponges should be placed conveniently for the anesthesiologist—who has the responsibility for determining blood loss—to see, and suggests that scales used to measure the weight of soiled surgical sponges should be protected from fluid accumulation, none of the procedures discussed lead to any apparatus by which a count may be easily made, details of the count entered, or blood loss determined, with a minimum of handling of the sponges, and using simple and very inexpensive equipment and disposable apparatus.

Other prior art, however, discloses proposals for handling surgical sponges, and certain kinds of apparatus which are available in the market.

For example, Dorton, in U.S. Pat. No. 3,749,237, issued July 31, 1973, teaches a bag strip for handling soiled surgical sponges, whereby a plurality of strips is formed on a roll of thermoplastic material, which strips are separated from the roll one at a time. Each strip is adapted to be hung from one of its ends, from any suitable support such as an intravenous pole, and a plurality of pouches is formed in the strip one under another. The pouches may either be small or large, the strip being formed with a central, easily rupturable, longitudinal seam from top to bottom, whereby small or large sponges may be accommodated and a sponge count made by inspection. The patent assumes that, especially when the strip is hung from an intravenous pole, a scale may also be provided.

However, use of the Dorton apparatus in an operating room requires that each of the soiled surgical sponges be removed from the kick bucket or elsewhere, and lifted up to the level of the opening of the next respective pouch into which that soiled sponge will be placed. That opening may be 10 or 20 cm. above the level of the top of the kick bucket, or it may be 100 or more cm. above the top of the kick bucket, because the pouches are formed one under another. Moreover, once the soiled sponge is placed in the pouch, as is clearly illustrated in the patent, the top of the pouch remains substantially open, so that there is still considerable risk of air-borne contamination coming from the soiled sponges.

At the completion of the surgical procedure, a sponge count can be determined by visual inspection. However, during the surgical procedure, if the sponge count is carried out periodically as suggested by Darden, the sponges are lifted from the kick bucket to the pouches, so that blood loss may be determined more or less accurately by the weight of the total number of soiled sponges at any moment less their unused standard weight, assuming there has been no evaporation or drying of the blood from the sponges in the meantime; or by a visual integration or "eyeball" determination of the amount of blood in the pouches and in each of the sponges, together with what may be still in the kick bucket.

A similar apparatus is also taught by Dorton in his U.S. Pat. No. 4,234,086, issued Nov. 18, 1980, where the capability of smaller pouches to be made into larger pouches to accommodate larger sponges, by rupturing a connection between the front and rear panels thereof, is emphasized. However, the bag mouth is not covered, although the gaping thereof is limited by the provision of other, rupturable, connections between the front and rear panels.

Olsen, in U.S. Pat. No. 4,190,153, issued Feb. 26, 1980, teaches a tray having a plurality of formed containers with a thin sheet material cover, and an access opening for each container through a pair of crossed slits. However, there is no easy determination of blood loss, and there is excessive handling of the soiled sponges.

A recently issued U.S. Pat. No. 4,295,537 to McAvinn et al, dated Oct. 20, 1981, shows a device for measuring sponges by which a plurality of wetted sponges is held by a retaining device applied to a measuring device, and the total weight of liquid in the sponges is thereafter calculated by a determining device. Once again, excessive handling of the sponges is required, with a lack of visibility by the operating room personnel.

The present invention overcomes those difficulties, by providing means whereby blood loss may be more easily determined—especially according to a particular corollary to the invention whereby the kick bucket is replaced with a transparent and disposable container—and as well, provides means whereby excessive handling of the soiled sponges is precluded; and also whereby the soiled sponges may be substantially covered after placement for counting, thereby reducing the rate at which they dry—and thereby assuring greater accuracy of determination of blood loss—as well as reducing the risk of air-borne contamination. Indeed, the present invention provides a self-contained system whereby soiled surgical sponges may be counted, weighed and disposed of, and the system is particularly such that blood loss may be quite accurately determined at almost any moment, and which may be operated in a manner discussed hereafter.

However, by the present invention, it is possible that the weight of the soiled sponges may be taken repeatedly before, during and after the counting procedure, so that by such techniques an accurate blood loss weight determination may be made.

In its most simple embodiment, the present invention provides an apparatus for handling soiled sponges from surgical procedures, which comprises a strip of thermoplastic material having a plurality of pouches formed therein. Each pouch is formed having a front and rear wall, a top, a bottom and opposed sides, and the front and rear walls of each of said pouches are securely sealed one to the other at the bottom of each pouch and at least at one side of each pouch. Each pouch has an opening at its top side, between the front walls, with each opening being substantially horizontal. The pouches are arranged so as to be contiguous one to another at at least one adjoining pair of sides, or an adjoining top and bottom, or both.

We have discovered, rather unexpectedly, that the provision of an apparatus for handling soiled surgical sponges is such that the sponge count during and after the surgical procedure may be made easier, and that a determination of blood loss may be made not only by visual inspection but by weighing the soiled sponges, with a reasonable degree of accuracy. Moreover, we have noted that the present invention provides a substantially self-contained system for counting, weighing and disposal of surgical sponges, which is such that each of the sponges need only be handled once after it has been discarded by the surgeon, or nurse.

In so doing, we therefore contemplate that the present invention may provide a continuous strip of arrays of pouches, such that the apparatus thereby provided may be hung around the very edge of the kick bucket—or other apparatus which is contemplated to replace the bucket—so that a minimum of physical transference of the soiled sponges occurs. Moreover, blood loss may be more easily determined, either visually or by use of a weighing system, when it is included in the sponge handling system apparatus.

The present invention therefore also contemplates a substantially self-contained system for counting, weighing and disposing of soiled surgical sponges, whereby a receptacle—preferably adapted to and associated with a frame for holding the same—is provided, together with the counter strip and a weighing scale or other weighing system, whereby blood loss during the operation may be monitored and determined simply by maintaining a record of sponges used and the weight of the soiled sponges less their unused weight. Moreover, the accuracy of determination of blood loss is increased by weighing a number of sponges at once, thus reducing any inherent error in the weighing system, by reducing the error per sponge being weighed.

By this invention, a very inexpensive product is made available, where an accurate sponge count and/or a blood loss determination may be made at any time.

Thus, the present invention provides an inexpensive and self-contained sponge handling, counting, weighing, documenting and disposal system, for use in operating rooms, with a greater degree of asepsis.

BRIEF DESCRIPTION OF THE DRAWINGS

These and other features and advantages of the present invention are more clearly described hereafter, in association with the accompanying drawings, in which:

FIG. 1 is a general view, broken in length, of one embodiment of a surgical sponge handling apparatus according to this invention;

FIGS. 2 and 3 are views which may be considered to have been taken in the direction of arrows A—A in FIG. 1, showing two different embodiments which each pouch of the apparatus of FIG. 1 may have;

FIG. 4 is a general, perspective view, showing how apparatus according to this invention may be used in a total system for counting, weighing and disposal of soiled surgical sponges;

FIG. 5 is a general view of an adapter ring intended for use with an ordinary kick bucket, in accordance with a feature of this invention.

DESCRIPTION OF THE PREFERRED EMBODIMENTS

As stated above, the present invention is particularly directed towards the provision of an apparatus for handling soiled sponges from surgical procedures, as well as to the provision of a system for counting, weighing and disposing soiled surgical sponges. The principal component of that system is the apparatus for handling soiled surgical sponges, including a sponge counter strip such as that designated at 10 in FIG. 1.

That apparatus comprises a strip 12 of thermoplastic material, which may have one or more arrays of pouches formed in it as discussed hereafter. Thus, there may be a plurality of pouches 14, or a plurality of pouches 16, or both, where the pouches 14 and/or 16 are formed in the strip 12. Each of the pouches 14 or 16 has a front wall and a rear wall, as described hereafter, and the front and rear walls of each of the pouches 14 and/or 16 are sealed one to the other at least along the bottom edges of each, as at 18 or 20, and along at least one side of each as at 22 or 24.

Each of the pouches 14 has an opening 26 at its top; and each of the pouches 16 has an opening 28 at its top. The openings 26 and 28 are opposite the bottoms 18 and 20, respectively, of pouches 14 and 16 and are all substantially horizontal.

In general, the strip of thermoplastic material 12 forms the rear wall of each of the pouches 14 and/or 16; however, the pouches may be formed by any convenient folding and sealing methods conventionally used in web handling of thermoplastic materials such as polyethylene, according to the ordinary skills of that art.

For example, as indicated in each of FIGS. 2 and 3, the strip 12 may form the rear wall of each of the pouches 30 or 32 of those figures, respectively. Pouch 30 is not unlike those which are indicated in FIG. 1, having a rear wall 34 and a front wall 36, where the rear and front walls 34 and 36 are sealed together at 38. In this embodiment, it is noted that a portion 36a of the front wall 36, extends through the rear wall 34 of the pouch; and the pouch 30 contains a soiled surgical sponge 40. (Of course, the portion 36a may also be inserted or tucked behind the soiled sponge 40.) The embodiment of FIG. 2 is arrived at by the provision of a plurality of apertures 42 or 44 in the strip 12, through which the top portions 46 or 48 of the pouches 14 and 16, respectively, may be inserted so as to take up the general appearance shown in FIG. 2. As seen, the soiled surgical sponge 40 is covered by the upper portion of the front wall 36 of the pouch 30, and it is clearly an easy matter to insert the soiled sponge 40 into the pocket and then simply press the upper part of the front wall of the pouch through the aperture, designated at 35 in FIG. 2.

In a different embodiment of the specific pouches formed in the apparatus according to the present invention, such as the pouch 32 of FIG. 3, the pouch again has a rear wall 50 and a front wall 52, sealed at 54. However, in this embodiment, there is a flap 56 which is sealed to the strip 12 at 58, and it overlies the top opening of the pouch 32. The flap 56 may be similar to that which covers a pocket in clothing, or it may be sealed at its edges such that the top portion of the front wall 52 of the pouch 32 must be tucked under the flap 56. In any event, it is once again clear that the soiled sponge 60 is covered after it has been placed in the pouch 32, so as to reduce air-borne contamination. Moreover, the rate at which the sponges may dry is reduced, thereby providing for greater accuracy of blood loss determination over a longer period of time.

As mentioned, several arrays of pouches may be provided. Moreover, the strip 12 may be formed with a perforated line along its length, as at 62, thus permitting separation of the array of pouches 16 from the array of pouches 14.

Moreover, pouch 16 may have a double pouch-like configuration, by having a partition formed in the front wall thereof by an indentation in the area indicated at 64. The pouch-like configuration of each of the contiguous pouches 16, formed in the front walls of each, may be formed of a particular size and/or configuration such that the front wall pouch configuration remain substantially unstressed except when a sponge larger than a pre-determined size may be placed into any of the pouches 16. Thus, a larger pouch—for example, as shown, twice the width of pouch 14—may be formed. Such pouches 16, when opened to their larger size, are convenient for placing laparotomy sponges therein.

Because of the necessity to keep accurate records of the surgical procedure, there may be provided on each strip 10 a portion 66 which is formed at one end thereof, substantially across the height of the strip 12. That portion 66 forms a data block, on which may be entered such information as the date, the sponge count, and such names as those of the patient, the surgeon, and the two persons who have each made an independent sponge count immediately prior to termination of the surgical procedure.

Still further, a tear-off strip 68 may be formed at one end of the strip 10—either at the same end as shown, or at the opposite end—and the tear-off strip 68 is also substantially across the height of the strip 12. In this case, the tear-off strip 68 provides a convenient means whereby, following the surgical procedure, the sponges and the disposable counter strip in whose pouches the sponges have been placed, may be tied together and disposed of.

In its most convenient form, the strip 10 may be provided at its top edge with means for suspending the strip. Such means may be a thicker portion—formed by sealing two or three layers of thermoplastic material together—as indicated at 70 in FIG. 2 or 3; or the sponge counter strip 10 may be suspended from eyelets 72 placed in the upper portion 74 and secured therein.

In any event, the sponge counter strip or sponge handling apparatus 10 is adapted along its top edge to be suspended from suspending means therefore.

Referring to FIG. 4, and in keeping with the system concept of the present invention, the sponge counter strip 10 may be associated with further means for suspending the sponge counter strip 10, such as pegs 76 which may be formed in specific operating room apparatus particularly designed for use with the sponge counter strip 10. The counter strip 10 may also be suspended from an adapter ring 96, such as is shown in FIG. 5, which may be fitted to the top edge of a standard kick bucket of the kind now usually found in operating rooms by clips 98 or other suitable means. The adapter ring 96 may also have the pegs 76 or other suitable suspending means for the counter strip, and may further have means for suspending a bag into the kick bucket as discussed hereafter.

In any event, it is convenient that a counting platform 78 should also be provided at the top of the kick bucket or receptacle, or on the adapter ring, so that the soiled sponges may be placed from the bottom of the kick bucket or receptacle, one at a time, on the counting platform 78 for further placement into the respective pouches of the counter strip 10. Likewise, the platform 78 may be formed on the adapter ring 96, as spoken of above.

Conveniently, the apparatus of FIG. 4 is provided with a wire frame which is substantially the same size of a standard kick bucket, and which is indicated at 80. The frame 80 is adapted to retain a clear plastic receptacle or bag 82 in its interior. Otherwise, the bag 82 may also be suspended into a kick bucket. Soiled surgical sponges 84 are shown in the bottom of the receptacle 82.

When the bag or receptacle 82 is clear, it is very easy for the operating room staff to at least make a visual determination of the amount of blood loss being incurred by the patient.

The apparatus of FIG. 4 is shown also with a number of soiled sponges 86 in the respective pouches which are formed in the sponge counter strip 10, with the strip being draped over the edge of the kick bucket or frame 80. Thus, it is seen that there is minimum handling of the soiled sponges once they are placed in the receptacle 82, and yet maximum opportunity is provided for all of the operating room staff to determine easily and visually the general amount of blood loss that the patient may be having.

Moreover, the present invention contemplates that the frame 80 and plastic receptacle 82 may be associated with a weighing apparatus 88, supported for example from below as at 90, so that manipulation of a convenient lever or others means 92 will cause a pointer 94 or other data display device of the weighing apparatus to provide an indication of the weight of the soiled sponges and thereby of the weight of fluid blood being lost by the patient. Of course, means are generally provided for setting a zero determination on the weighing apparatus 88, or for deducting the tare weight of the frame 80 and receptacle 82, and strip 10, so that only the weight of the soiled sponges is indicated. Especially when a wire frame 80 is used, the tare weight is lower, so that a more senstive weighing apparatus may be used. Also, of course, and as previously noted, the use of the wire frame 80 and receptacle 82 provides a maximum visibility of blood loss, etc. as the soiled sponges are placed into the receptacle.

Indeed, a calculating weighing device may be provided, so that by entry of the number of sponges in the respective pouches of the counter strip and/or in the bottom of the receptacle 82, an exact reading of actual weight of fluid blood loss may be determined; and if a printing unit is included, a print-out of the data may be obtained for the later purpose of varifying the sponge count. Moreover, a chart may also be provided, on which there may continually be placed entries such as the number of dry and wet—i.e., with saline solution—sponges of each size being used may be entered, together with either a running count of the number of sponges being used or of the number of sponges yet unused—or both—, whereby at any time the total weight of soiled sponges may be determined. From that total weight, may be deducted the unused weights of the ponges—determined either by the running count or subtraction from the number of sponges in the operating room before the surgical procedure of the number of unused sponges or sponges still in use by the surgeon—whereby the anestheologist who has the responsibility for determining blood loss may obtain such information without an actual count having been made into other containers which would then have to be weighed. Of course, sponge counts are made for verification and procedural documentation, but the system as contemplated herein provides an accurate determination of blood loss during the surgical procedure, at any moment, without excessive handling of the sponges.

The AORN article referred to above stresses that all items that are in or come into contact with the patient and/or the sterile field, must be considered to be contaminated, and that every effort should be made to confine the contamination to the area immediately surrounding the sterile field. It follows that all contaminated items, and especially soiled surgical sponges, should be handled as little as possible.

Thus, one of the advantages of the present invention comes from the fact that the receptacle 82 into which the soiled sponges coming from the field of the operation (the sterile surgical area) is first discarded, is generally also the same container within which the soiled sponges are ultimately disposed of. There is therefore a self-contained system for retaining, weighing, counting and disposing of surgical sponges. By this invention, therefore, there is no loss of blood due to the handling and transference from the first receptacle (the kick bucket) to another separate device or container for purposes of weighing or counting, as has previously been the case, and therefore more accurate determination of blood lost by the patient during surgery is possible. Still further, the accuracy of blood loss determination may be enhanced because any error which occurs in the weighing system is less per sponge when a greater number of sponges is weighed at any given time, thus reducing the percentage error of the weighing system.

Generally, the surgical sponge counter strip according to this invention is provided in such a manner that the pouches are formed so as to have some depth from front to back wall, and are thereby more readily adapted to accommodating soiled surgical sponges when placed therein.

Especially when the apparatus is provided with a receptacle 82 which first receives the soiled sponges, after which they are counted into the counter strip, so that a final sponge count may be readily determined, the sponge counter strip 10 may thereafter be returned to the receptacle 82 so that the entire bag or receptacle 82 and sponge counter strips 10 and the contained soiled sponges may be disposed of merely by disposing of the bag 82.

However, as noted, the sponge counter strips 10 may be provided in such a manner that the lower array of pouches (when present) may be separated from the upper array of pouches, especially when large surgical sponges are placed therein, so that those large surgical sponges may be recovered and re-used.

The surgical sponge counter strips 10, according to the present invention, are preferably formed so as to be dispensed one at a time from a suitable dispensing package or container.

In any event, it is seen that, by the provision of apparatus according to the present invention, an entirely self contained system may be provided for handling, counting, weighing and disposing of soiled surgical sponges. Moreover, according to the present invention, the apparatus is such that there is no excessive handling of the sponges, such that it is not necessary to lift the sponges from near floor level to near eye level to place any one sponge in a respective counter pouch.

Still further, it is evident that all of the sponges being used during any surgical procedure may be kept together for a visual determination of blood loss, and for weighing to obtain a more accurate determination of the weight of fluid blood loss. Even further, when the sponges are covered—either by inserting a flap through an aperture formed in the rear wall of each pouch, or by a flap which overlays the opening of each pouch—not only is there a reduced risk of microbial contamination, there may also be less risk of the sponges drying out and therefore a more accurate weight-determination of blood loss.

The provision of the data strip 66 is such that full documentation is available at all times, and the data strip 66 may be retained outside of the bag or disposable container into which the filled counter strips 10 with their soiled surgical sponges may be placed.

As noted, as adaptor ring 96 may be provided having a counting platform 78, and being adjustable to fit kick buckets already in use in an operating room, and having pegs or other suspending arrangement for suspending and retaining the sponge counter strips 10 so as to minimize handling of the soiled surgical sponges.

It is evident that many specific embodiments of the pouches may be provided, having various means for covering the soiled sponges once they have been placed into each respective pouch. Moreover, it is especially to be noted that the apparatus of the present invention, provides a more efficient handling of soiled surgical sponges with less risk of air-borne microbial contamination, and with a minimum of physical transference of the soiled sponges, and yet assuring an accurate sponge count by the placement of sponges in their respective pouches. As noted, some pouches may be provided whereby their size may be increased so as to dispose of larger sponges.

Preferably, the thermoplastics material of the sponge counter strip according to the present invention is a clear yet strong material such as polyethylene. In any event, any suitable material may be used, and any specific design of the pouch configuration and cover therefor provided, as well as the provision of means for suspending the apparatus for handling soiled sponges in an entire weighing, counting and disposal system therefor, without departing from the spirit and scope of the appended claims.

What is claimed is:

1. A system for collecting, containing, counting, weighing and disposing of soiled sponges from surgical procedures, comprising:
    means for suspending and retaining a disposable receptacle into which said soiled sponges may be placed directly from the field of operation;
    a strip of thermoplastic material having a plurality of pouches formed therein, each pouch having front and rear walls and having a top, a bottom and a pair of opposed sides; the front and rear walls of each pouch being securely sealed one to the other at the bottom and at least one side thereof, and having a substantially horizontal opening between said front and rear walls at its top side; said plurality of pouches being contiguous one to another at at least one adjoining pair of sides, or at a respective top and bottom of adjoining pouches;
    and means for suspending said strip of thermoplastic material from its top edge; and means for weighing at least said receptacle, said strip of thermoplastic material, said suspending means and any soiled surgical sponges contained in said pouches.

2. The apparatus of claim 1, where said receptacle is adapted for suspension within a wire frame associated with said weighing means.

3. The apparatus of claim 1 or 2, further comprising platform means above said receptacle, onto which soiled surgical sponges may be placed.

4. The apparatus of claim 1 or 2, further comprising a calculating weighing device for giving an indication of the weight of fluid retained in said soiled sponges in said pouches, by entry of appropriate data as to the number and type of sponges being contained in said pouches.

5. The apparatus of claim 1 or 2, further comprising platform means above said receptacle, onto which soiled surgical sponges may be placed and a calculating weighing device for giving an indication of the weight of fluid retained in said soiled sponges in said pouches, by entry of apropriate data as to the number and type of sponges being contained in said pouches.

6. The apparatus of claim 1, 2 or 3, where said thermoplastic strip material is adapted along its top edge to be suspended from suspending means therefor.

7. The apparatus of claim 1, 2 or 3, further comprising means for suspending said apparatus from its top edge, said top edge being adapted for suspension from said suspending means; said suspending means being adapted to fit standard operating room kick buckets or other standard operating room receptacles for soiled surgical sponges.

8. The apparatus of claim 1, 2 or 3, further comprising means for suspending said apparatus from its top edge, said top edge being adapted for suspension from said suspending means; and further comprising means for weighing said suspending means, and said apparatus and soiled sponges contained in the pouches thereof.

* * * * *